(12) United States Patent
Neumann

(10) Patent No.: US 11,107,555 B2
(45) Date of Patent: Aug. 31, 2021

(54) METHODS AND SYSTEMS FOR IDENTIFYING A CAUSAL LINK

(71) Applicant: KPN INNOVATIONS, LLC, Lakewood, CO (US)

(72) Inventor: Kenneth Neumann, Lakewood, CO (US)

(73) Assignee: KPN INNOVATIONS, LLC, Lakewood, CO (US)

(*) Notice: Subject to any disclaimer, the term of this patent is extended or adjusted under 35 U.S.C. 154(b) by 0 days.

(21) Appl. No.: 16/590,417

(22) Filed: Oct. 2, 2019

(65) Prior Publication Data
US 2021/0104300 A1    Apr. 8, 2021

(51) Int. Cl.
| | | |
|---|---|---|
| G16B 40/20 | (2019.01) | |
| G06N 7/00 | (2006.01) | |
| G16H 80/00 | (2018.01) | |
| G16H 10/60 | (2018.01) | |

(52) U.S. Cl.
CPC .......... *G16B 40/20* (2019.02); *G06N 7/005* (2013.01); *G16H 10/60* (2018.01); *G16H 80/00* (2018.01)

(58) Field of Classification Search
CPC .......... G16B 40/20; G16B 40/30; G16B 5/20; G16H 50/20; G16H 50/70; G16H 10/40; G16H 10/60; G16H 80/00; G06F 19/325; G06F 16/285; A61B 5/7264; A61B 5/7267; G06N 7/005; G06N 20/00; G06N 3/02; G06N 3/0472; G06N 3/08
See application file for complete search history.

(56) References Cited

U.S. PATENT DOCUMENTS

| | | | |
|---|---|---|---|
| 2009/0024356 A1 | 1/2009 | Platt et al. | |
| 2014/0195168 A1 | 7/2014 | Shaikh | |
| 2016/0171383 A1 | 6/2016 | Narain et al. | |
| 2017/0372443 A1* | 12/2017 | Katsuda | G16H 70/60 |
| 2018/0011972 A1* | 1/2018 | Rajan | G06F 16/9024 |
| 2018/0166174 A1 | 6/2018 | Lewis | |

(Continued)

OTHER PUBLICATIONS

Blessia et al; "Application of Knowledge Based Systems for Diagnosis of Osteoarthritis"; Apr. 2011; https://www.researchgate.net / publication/283253515_Application_of_Knowiedge_Based_System_ for_Diagnosis_of_Osteoarthritis.

*Primary Examiner* — Kamran Afshar
*Assistant Examiner* — Marshall L Werner
(74) *Attorney, Agent, or Firm* — Caldwell Intellectual Property Law, LLC

(57) ABSTRACT

A system for identifying a causal link, the system including a diagnostic generator module configured to receive a first user symptom datum, receive diagnostic training data, and generate using a supervised machine-learning process a diagnostic model that outputs a first prognosis. The system includes a prognostic chaining module configured to receive an expert input dataset, receive the first user symptom datum and the first prognosis, generate a gaussian mixture clustering model and identify a first causal link chained to the first prognosis. The system includes a causal link module configured to receive the first prognosis chained to the first causal link, receive a second prognosis chained to a second causal link, and evaluate the first causal link and the second causal link to calculate a degree of similarity between the first causal link and the second causal link.

20 Claims, 9 Drawing Sheets

(56) References Cited

U.S. PATENT DOCUMENTS

| | | |
|---|---|---|
| 2018/0307995 A1 | 10/2018 | Conroy et al. |
| 2018/0315488 A1* | 11/2018 | Miranda ................ G16H 10/60 |
| 2019/0027249 A1 | 1/2019 | Fuksenko et al. |
| 2019/0035504 A1 | 1/2019 | Jang |
| 2019/0057774 A1 | 2/2019 | Velez et al. |
| 2019/0108912 A1 | 4/2019 | Spurlock, III et al. |
| 2019/0119730 A1* | 4/2019 | Spurlock, III ....... C12Q 1/6809 |
| 2019/0147352 A1 | 5/2019 | Ovsak |
| 2019/0154707 A1* | 5/2019 | Flamini .................. G01N 30/02 |
| 2019/0214138 A1* | 7/2019 | Aoyagi .................. G16H 50/20 |
| 2019/0235836 A1* | 8/2019 | Boehm ..................... G06F 1/30 |
| 2019/0310269 A1* | 10/2019 | Cirulli ................ G01N 33/6893 |

* cited by examiner

METHODS AND SYSTEMS FOR IDENTIFYING A CAUSAL LINK

FIELD OF THE INVENTION

The present invention generally relates to the field of artificial intelligence. In particular, the present invention is directed to methods and systems for identifying a causal link.

BACKGROUND

Accurate identification of causal links can be challenging. Frequently, practitioners are unaware of a root cause that may ultimately be attributing to a symptom. Further, this problem is exacerbated by the plethora of medical literature available that practitioners often lack adequate time to read and analyze.

SUMMARY OF THE DISCLOSURE

In an aspect, a system for identifying a causal link is presented. The system includes a computing device wherein the computing device further comprises one or more network interfaces and one or more processors. The system includes a diagnostic generator module operating on the at least a computing device, the diagnostic generator module designed and configured to receive a first user symptom datum from a user client device wherein the first user symptom datum includes a current medical indicator; receive diagnostic training data from a machine-learning database correlating symptom data to prognostic data; and generate using a supervised machine-learning process a diagnostic model that receives the first user symptom datum as an input and produces an output containing a first prognosis. The system includes a prognostic chaining module operating on the computing device, the prognostic chaining model designed and configured to receive an expert input dataset from an expert knowledge database wherein the expert input dataset further comprises prognostic data correlated to causal link data; receive the first user symptom datum and the first prognosis from the diagnostic generator module; generate a gaussian mixture clustering model utilizing the expert input dataset and the first prognosis and outputting a defined number of clusters; and identify a first causal link chained to the first prognosis as a function of generating the gaussian mixture clustering model. The system includes a causal link module operating on the computing device the causal link module designed and configured to receive from the prognostic chaining module the first prognosis chained to the first causal link; receive from the prognostic chaining module a second prognosis chained to a second causal link; and evaluate the first causal link and the second causal link to calculate a degree of similarity between the first causal link and the second causal link.

In an aspect, a method of identifying a causal link includes receiving by a computing device a first user symptom datum from a user client device wherein the first user symptom datum includes a current medical indicator. The method includes receiving by the computing device diagnostic training data from a machine-learning database correlating symptom data to prognostic data. The method includes generating by the computing device using a supervised machine-learning process a diagnostic model that receives the first user symptom datum as an input and produces an output containing a first prognosis. The method includes receiving by the computing device an expert input dataset from an expert knowledge database wherein the expert input dataset further comprises prognostic data correlated to causal link data. The method includes generating by the computing device a gaussian mixture clustering model utilizing the expert input dataset and the first prognosis and outputting a defined number of clusters. The method includes identifying by the computing device a first causal link chained to the first prognosis as a function of generating the gaussian mixture clustering model. The method includes receiving by the computing device a second prognosis chained to a second causal link. The method includes evaluating by the computing device the first causal link and the second causal link to calculate a degree of similarity between the first causal link and the second causal link.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
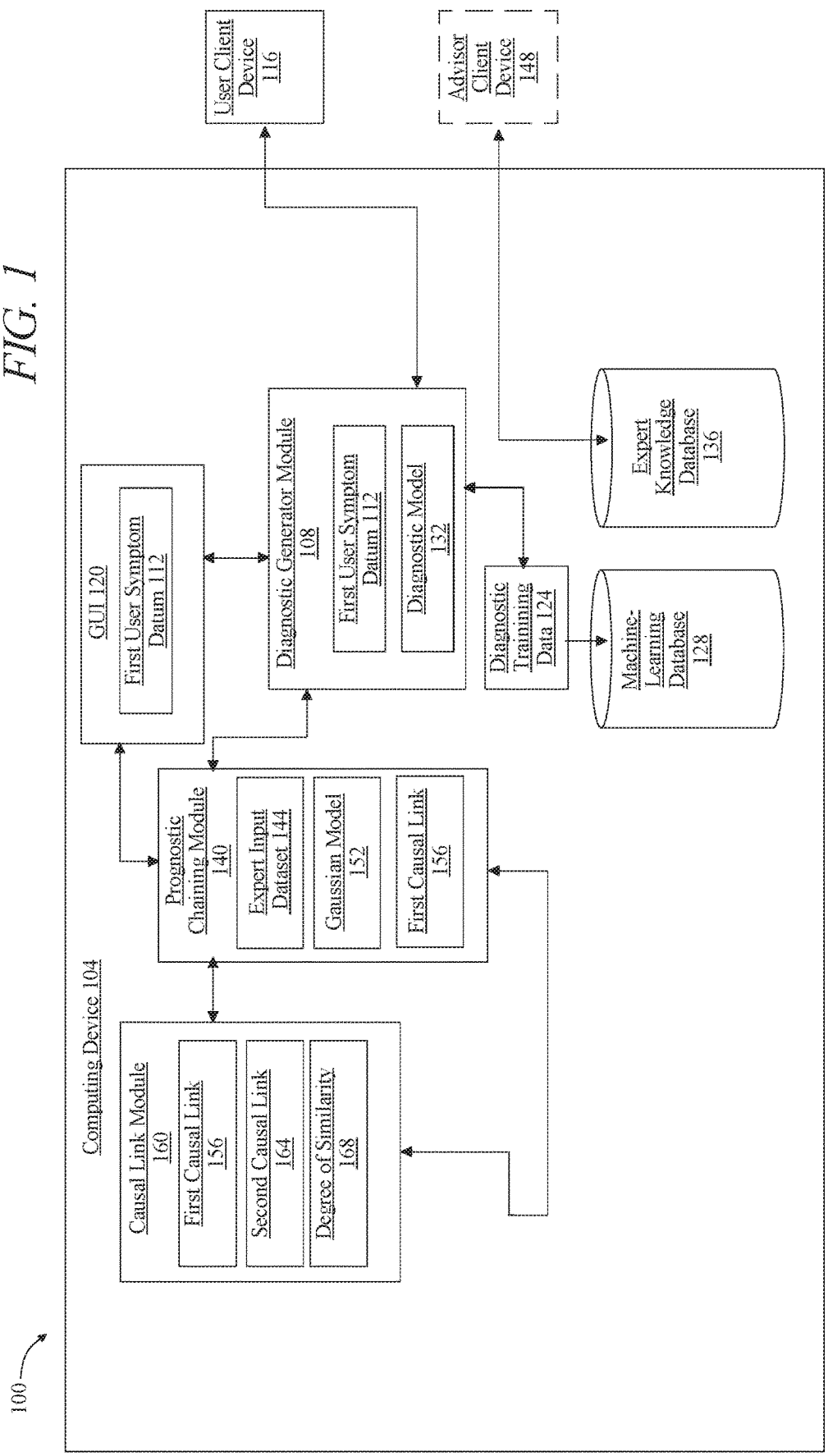
FIG. 1 is a block diagram illustrating an exemplary embodiment of a system for identifying a causal link.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for identifying a causal link. In an embodiment, a computing device includes a diagnostic generator module that receives a first user symptom datum from a user client device wherein the first user symptom datum includes a current medical indicator. The system receives diagnostic training data correlating symptom data to prognostic data and generates using a supervised machine-learning process a diagnostic model that produces an output containing a first prognosis. The system includes a prognostic chaining module that receives an expert input dataset that includes prognostic data correlated to causal link data. The prognostic chaining module generates a gaussian mixture clustering model and identifies a first causal link chained to the first prognosis. The system includes a causal link module configured to receive the first prognosis chained to the first causal link and receive a second prognosis chained to a second causal link. The causal link module evaluates the first causal link and the second causal link to calculate a degree of similarity between the first causal link and the second causal link.

System 100 includes at least a computing device 104, wherein the at least a computing device 104 further comprises one or more network interfaces, a non-volatile memory, and including one or more processors. Computing device 104, as used herein, includes any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include at least a server. At least a server may include a single computing device 104 operating independently or may include two or more computing device 104 operating in concert, in parallel, sequentially or the like; two or more computing device 104 may be included together in a single computing device 104 or in two or more computing device 104. At least a server may interact with one or more additional devices as described below in further detail via a network interface device. Network interface device may be utilized for connecting at least a server to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device 104, and any combinations thereof. A network may employ a wired and/or a wireless mode of communication. In general, any network topology may be used. Information (e.g., data, software etc.) may be communicated to and/or from a computer and/or a computing device 104. At least a server may include but is not limited to, for example, a computing device 104 or cluster of computing device 104 in a first location and a second computing device 104 or cluster of computing device 104 in a second location. At least a server may include one or more computing device 104 dedicated to data storage, security, distribution of traffic for load balancing, and the like. At least a server may distribute one or more computing tasks as described below across a plurality of computing device 104 of computing device 104, which may operate in parallel, in series, redundantly, or in any other manner used for distribution of tasks or memory between computing device 104. At least a server may be implemented using a "shared nothing" architecture in which data is cached at the worker, in an embodiment, this may enable scalability of system 100 and/or computing device 104.

With continued reference to FIG. 1, at least a computing device 104 may be designed and/or configured to perform any method, method step, or sequence of method steps in any embodiment described in this disclosure, in any order and with any degree of repetition. For instance, at least a computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 includes a diagnostic generator module 108 operating on at least a computing device. Diagnostic generator module 108 may include any hardware and/or software module. Diagnostic generator module 108 is configured to receive a first user symptom datum 112 from a user client device 116 wherein the first user symptom datum 112 includes a current medical indicator. A "first user symptom datum" as used in this disclosure, an element of data describing information relevant to human subject's state of health, including without limitation symptoms, conditions, prognoses, test results, concerns, reasons for a visit to a healthcare professional, personal stories and/or information concerning the human subject's interests, relationships to other people, informal and/or formal personal or health support groups or persons, or the like. A first user symptom datum 112 includes a current medical indicator. A "current medical indicator" as used in this disclosure, includes an element of data describing any subjective description of a current or future probable disease that a user is experiencing. Subjective descriptions may include any phenomenon a user may be experiencing including for example anxiety, pain, fatigue, tremor, headache and the like. A first user symptom datum 112 may be apparent as indicating a particular condition and/or disease such as when a user experiences blood loss from a subcutaneous flesh would. A first user symptom datum 112 may not be apparent as indicating a particular condition and/or disease such as when a user may experience tiredness due to a thyroid disease which a user may believe is due to being overly fatigued. A "disease" as used in this disclosure, includes an abnormal condition that negatively affects the structure and/or function of part of a human body. A disease may include a current disease diagnosed by a health professional who may be authorized by a particular health licensing board to diagnose disease and/or conditions such as for example a medical doctor, a doctor of osteopathy, a nurse practitioner, a physician assistant, a doctor of optometry, a doctor of dental medicine, a doctor of dental surgery, a naturopathic doctor, a doctor of physical therapy, a nurse, a doctor of chiropractic medicine, a doctor of oriental medicine, and the like. A disease may include a future probable disease identified by the presence of one or more predisposing factors. Predisposing factors may include genetic predispositions such as a genetic characteristic which influences the possible phenotypic development of a disease. For instance and without limitation, a genetic characteristic such as a mutation of breast cancer gene 1 (BRCA1) may predispose a user to have a predisposition to develop certain cancers such as breast and ovarian cancer. Predisposing factors may include behavior predispositions such as negative behaviors that may predispose a user to certain future probable diseases. For example, a negative behavior such as smoking may predispose a user to lung cancer while a negative behavior such as eating foods high in saturated fats may predispose a user to heart disease.

With continued reference to FIG. 1, diagnostic generator module 108 receives a first user symptom datum 112 from a user client device 116. User client device 116 may include, without limitation, a display in communication with computing device, display may include any display as described herein. User client device 116 may include an additional computing device, such as a mobile device, laptop, desktop computer, or the like; as a non-limiting example, user client device 116 may be a computer and/or workstation operated by a medical professional. Medical professional may include any of the medical professionals as described herein. Output may be displayed on a user client device 116 using an output graphical user interface 120.

With continued reference to FIG. 1, graphical user interface 120 may include without limitation, a form or other graphical element having data entry fields, wherein a user may enter a user symptom datum. Graphical user interface 120 may include data entry fields that allow for a user to enter free form textual inputs. Graphical user interface 120 may provide drop-down lists, where users may be able to select one or more entries to indicate one or more user symptom datums.

With continued reference to FIG. 1, diagnostic generator module 108 is configured to receive diagnostic training data 124 from a machine-learning database 128 correlating symptom data to prognostic data. "Training data," as used in this disclosure, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by at least a server may correlate any input data as described in this disclosure to any output data as described in this disclosure.

With continued reference to FIG. 1, diagnostic generator module 108 receives training data correlating symptom data to prognostic data. "Correlation" in a training data set may include any relation established therein linking one datum to another, including inclusion together in a data element, row, column, cell, or the like, and/or by giving each a common indicator and/or label indicative of their correlation in data used to create and/or compile training data. Correlation may include a relation established whereby symptom data is correlated to prognostic data based on data entries obtained from the same subject. Training set may include a plurality of entries, each entry correlating at least an element of symptom data to prognostic data.

With continued reference to FIG. 1, "prognostic data" as used in this disclosure, includes an element of data identifying and/or describing a current, incipient, or probable future medical condition affecting a person; medical condition may include a particular disease, one or more symptoms associated with a syndrome, a syndrome, and/or any other measure of current or future health and/or healthy aging. Prognostic data may be associated with a physical and/or somatic condition affecting human health. Conditions may include for example, one or more diseases, defined herein as conditions that negatively affect structure and/or function of part or all of an organism. Conditions associated with prognostic data may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Prognostic data may be associated with one or more immune disorders, including without limitation immunodeficiencies and/or auto-immune conditions. Prognostic data may be associated with one or more metabolic disorders. Prognostic data may be associated with one or more endocrinal disorders. Prognostic data may be associated with one or more cardiovascular disorders. Prognostic data may be associated with one or more respiratory disorders. Prognostic data may be associated with one or more disorders affecting connective tissue. Prognostic data may be associated with one or more digestive disorders. Prognostic data may be associated with one or more neurological disorders such as neuromuscular disorders, dementia, or the like. Prognostic data may be associated with one or more disorders of the excretory system, including without limitation nephrological disorders. Prognostic data may be associated with one or more liver disorders. Prognostic data may be associated with one or more disorders of the bones such as osteoporosis. Prognostic data may be associated with one or more disorders affecting joints, such as osteoarthritis, gout, and/or rheumatoid arthritis. Prognostic data be associated with one or more cancers, including without limitation carcinomas, lymphomas, leukemias, germ cell tumor cancers, blastomas, and/or sarcomas. Prognostic data may include descriptors of latent, dormant, and/or apparent disorders, diseases, and/or conditions. Prognostic data may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic data as described in this disclosure.

With continued reference to FIG. 1, diagnostic training data 124 may be received from machine-learning database 128. Machine-learning database 128 may include any data structure suitable for ordered storage and retrieval of data, which may be implemented as a hardware or software module. Machine-learning database 128 may be implemented, without limitation, as a relational database, a key-value retrieval datastore such as a NOSQL database, or any other format or structure for use as a datastore that a person skilled in the art would recognize as suitable upon review of the entirety of this disclosure.

With continued reference to FIG. 1, diagnostic generator module 108 is configured to generate using a supervised machine-learning process a diagnostic model 132 that receives the first user symptom datum 112 as an input and produces an output containing a first prognosis. Supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of symptom data as inputs, prognostic data as outputs, and a scoring function representing a desired form of relationship to be detected between elements of symptom data and prognostic data; scoring function may, for instance, seek to maximize the probability that a given element of symptom data is associated with given prognostic data and/or combination of prognostic data to minimize the probability that a given element of symptom data and/or combination of elements of symptom data is not associated with given prognostic data and/or combination of prognostic data. Scoring function may be expressed as a risk function representing an "expected loss" of an algorithm relating inputs to outputs, where loss is computed as an error function representing a degree to which a prediction generated by the relation is incorrect when compared to a given input-output pair provided in a training set. Persons skilled in the art, upon reviewing the entirety of this disclosure, will be aware of various possible variations of supervised machine-learning algorithms that may be used to determine relation between elements of symptom data and prognostic data. In an embodiment, one or more supervised machine-learning algorithms may be restricted to a particular domain for instance, a supervised machine-learning process may be performed with respect to a given set of parameters and/or categories of parameters that have been suspected to be related to a given set of symptom data, and/or are specified as linked to a medical specialty and/or field of medicine covering a particular set of prognostic data. As a non-limiting example, a particular set of symptoms may be typically used by endocrinologists to diagnose or predict various endocrine conditions, and a supervised machine-learning process may be performed to relate those symptoms to the various prognostic data; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate diagnostic data. Additional supervised learning processes may be performed without domain restrictions to detect, for instance, previously unknown and/or unsuspected relationships between diagnostic data and prescriptive elements.

With continued reference to FIG. 1, diagnostic generator module 108 is configured to generate using a supervised machine-learning processes a diagnostic model 132 that outputs a first prognosis. Supervised machine-learning processes may include classification algorithms, defined as processes whereby a computing device 104 derives, from training data, a model for sorting inputs into categories or bins of data. Classification may be performed using, without limitation, linear classifiers such as without limitation logistic regression and/or naive ve Bayes classifiers, nearest neighbor classifiers, support vector machines, decision trees, boosted trees, random forest classifiers, and/or neural network-based classifiers.

Still referring to FIG. 1, machine-learning processes as described in this disclosure may be used to generate machine-learning models. A "machine-learning model," as used in this disclosure, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning, for instance for multi-layered networks.

With continued reference to FIG. 1, diagnostic generator module 108 is configured to receive a first user blood test indicating at least a measure of user genetic data. A "first user blood test" as used in this disclosure, includes a blood sample that is extracted from a user and analyzed for an element of user genetic data. "User genetic data" as used herein is a sample including any sequence of nucleic acid identified in a user, including without limitation deoxyribonucleic acid (DNA) and/or ribonucleic acid (RNA). DNA may include chromosomal DNA, including without limitation sequences encoding particular genes as well as sequences of DNA disposed between or after gene sequences, including without limitation telomeres. Telomeres, as used in this description are caps (repetitive nucleotide sequences) at the end of linear chromosomes of a user. Telomeres are theorized to play a critical role in facilitating complete chromosome replication. Telomeres are characterized by noncoding tandem arrays of a "TTAGGG" DNA sequence that are located at the terminal ends of all vertebrate chromosomes, including those of humans. A G-rich single stranded 3-prime overhang is present at the end of human telomeres; this overhang, which may be important for telomere function folds back on itself forming a large loop structure called a telomere loop, or T-loop, that has a shape similar to that of a paper clip. A telomere may be stabilized by a six-protein complex, known as "shelterin," which may include telomeric repeat binding factor 1 and 2 (TRF1 and TRF2), protection of telomeres 1 (POT1), TRF1 and TRF2 interacting nuclear protein 2 (TIN2), the human ortholog of the yeast repressor/activator protein 1 (Rap1), and TPP1. Telomere lengths have been observed to reduce over a series of cellular mitotic divisions, such that telomere length and/or changes in telomere length appear to correlate with processes of cellular aging and senescence. It is therefore hypothesized that telomere length and/or changes thereto may be useful to predict life expectancy of a person; however, precise predictions have hitherto eluded researchers. A genetic sample may include mRNA, tRNA, or any other RNA sequence or strand.

With continued reference to FIG. 1, genetic data may be extracted from a user by a physically extracted sample. Physically extracted sample may include without limitation a tissue sample, a buccal swab, a fluid sample, a chip and/or microchip embedded under the skin, a biopsy or the like. Extraction of genetic samples may be performed using any suitable physical process, including separation of nucleic acid from other tissue and/or fluid elements using, without limitation, a centrifuge. Extraction may include any form of restriction or division of a DNA and/or RNA sequence into sub-sequences, including without limitation using restriction enzymes. Extraction of genetic samples may include one or more variations of polymerase chain reaction "PCR" processes, whereby a particular strand of nucleic acid is replicated or "amplified" in a solution of nucleic acid by repeatedly exposing the solution to stimulus, such as heat, that breaks base-pair bonds, and then removing the stimulus to allow base-pair bonds to reform; as a result, a strand or sequence of nucleic acid will bond to free-floating molecules of nucleic acid, forming an inverse copy of itself, which will be separated from the strand or sequence during stimulus, and subsequently each of the strand and the inverse copy will bond to further free-floating molecules. As the above-described process is repeated, the number of copies of the strand or sequence increases exponentially. Extraction may include any suitable process to measure sequence lengths, match sequences, or the like, including without limitation electrophoresis.

With continued reference to FIG. 1, diagnostic generator module 108 receives genetic training data from machine-learning database 128 correlating genetic data to prognostic data. Genetic data may include any of the genetic data as described above. Prognostic data may include any of the prognostic data as described above. Genetic training data may be stored in machine-learning database 128 as described above in more detail. Diagnostic generator module 108 generates using a supervised machine-learning process a genetic model that receives first user genetic data as an input and produces an output containing a first prognosis. Supervised machine-learning process may include any of the supervised machine-learning processes as described above. Generating genetic model may be performed utilizing any of the methods for generating diagnostic model 132 as described above. First prognosis may include any of the first prognosis as described above.

With continued reference to FIG. 1, diagnostic generator module 108 is configured to receive a second user symptom datum from a user client device 116 wherein the second user symptom datum includes a current medical indicator. Second user symptom datum may include any user symptom datum suitable for use as first user symptom datum 112. In an embodiment, second user symptom datum may be unrelated and a separate symptom from first user symptom datum 112. For instance and without limitation, first user symptom datum 112 may include a user complaint of cold hands while a second user symptom datum may include a user complaint of back pain. In an embodiment, second user symptom datum may be related to a first user symptom datum 112. For instance and without limitation, a first user symptom datum 112 such as a stomachache may be related to a second user symptom datum such as diarrhea. A first user symptom datum 112 may be related to a second user symptom datum when the same body system and/or location on the body are impacted. Diagnostic generator module 108 is configured to receive diagnostic training data 124 from machine-learning database 128 correlating symptom data to prognostic data and generate using a supervised machine-learning process a diagnostic model 132 that receives the second user symptom datum as an input and produces an output containing a second prognosis. Supervised machine-learning process may include any of the supervised machine-learning processes as described above.

With continued reference to FIG. 1, system 100 includes a prognostic chaining module 140 operating on the computing device. Prognostic chaining module 140 may include any hardware and/or software module. Prognostic chaining module 140 is configured to receive an expert input dataset 144 from an expert knowledge database 136 wherein the expert input dataset 144 further comprises prognostic data correlated to causal link data. An "expert input dataset" as used in this disclosure, includes expert submissions from expert authorities describing prognostic data correlated to causal link data. Expert authorities may include functional medicine health professionals such as doctors, nurse practitioners, physician assistants, and the like who may practice a particular sect of functional medicine and who may be considered a leading authority in his or her field of expertise. Expert authorities may have particular credentials, training and/or experience to be considered an expert in a field. For example, expert authorities may include experts who have certifications issued by THE INSTITUTE FOR FUNCTIONAL MEDICINE of Federal Way, Wash. In yet another non-limiting example, expert authorities may include experts who have certifications issued by AMERICAN ACADEMY OF ANTI-AGING MEDICINE (A4M) OF Boca Raton, Fla. Expert submissions may include datasets describing particular diagnoses and known causal links or root causes of diagnoses. Root cause of disease includes a holistic approach that addresses the underlying cause of a disease or diagnosis as opposed to a particular treating a symptom of a disease. For instance and without limitation, an expert submission may describe a blocked artery as having a root cause of high inflammation. In yet another non-limiting example, an expert submission may describe a headache experienced repeatedly before menstruation as having a root cause of low progesterone.

With continued reference to FIG. 1, expert submissions may be entered by an expert and stored within expert knowledge database 136. Expert knowledge database 136 may include any data structure suitable for use as machine-learning database 128. Expert knowledge database 136 may store and/or organize expert submissions. In an embodiment, expert knowledge database 136 may store expert submissions by prognosis and/or causal link data as described in more detail below. Expert submissions may include textual entries from journals and/or research papers as described in more detail below.

With continued reference to FIG. 1, expert submissions may be entered into expert knowledge database 136 by an expert using an advisor client device 148. Advisor client device 148 may include any device suitable for use as a user client device 116 as described above. Advisor client device 148 may include a graphical user interface 120 whereby an expert may enter expert inputs. Graphical user interface 120 may include any of the graphical user interfaces 120 suitable for use on user client device 116 as described above. In an embodiment, advisor client device 148 may include a graphical user interface 120 whereby an expert may enter expert inputs. Graphical user interface 120 may include free form textual inputs and/or a drop down menu whereby an expert may select an option.

With continued reference to FIG. 1, prognostic chaining module 140 is configured to generate a gaussian mixture clustering model 152 utilizing the expert input dataset 144 and the first prognosis. Gaussian mixture clustering model 152 includes a clustering algorithm that utilizes expert input dataset to generate Gaussian mixture clustering model 152. An "expert input dataset" as used in this disclosure, includes a collection of one or more datapoints. A "data point" as used in this disclosure, includes a single data entry. Gaussian mixture clustering model 152 may assume that data points contained within a dataset are Gaussian distributed whereby two parameters may be utilized to describe the shape of clusters generated by Gaussian mixture model that include a mean value parameter and a standard deviation value parameter. To calculate mean value parameter and standard deviation value prognostic chaining module 140 may generate expectation-maximization (EM) algorithm. Generating EM algorithm may include first selecting a set number of clusters. Prognostic chaining module 140 may select a number of clusters by consulting expert knowledge database 136. Experts may provide input as to what expert datasets are best suited for a particular number of clusters. For instance and without limitation, an expert dataset relating to a causal link for a prognostic label such as Lyme Disease may be best suited for an output using EM algorithm to generate thirteen clusters while an expert dataset relating to a causal link for a prognostic label such as osteoarthritis may be best suited for an output using EM algorithm to generate three clusters. After set number of clusters to output has been determined, Gaussian distribution may be initialized for each cluster and each parameter. After Gaussian distribution for each cluster and each parameter has been calculated, generating EM algorithm may next involve computing the probability that each datapoint belongs to a particular cluster. EM algorithm may assume that the closer a datapoint is to the Gaussian's center, the more likely it belongs to that cluster. Based on these probabilities, the EM algorithm computes a new set of parameters for the Gaussian distributions so that probabilities of datapoints within each cluster are maximized. This may be performed by calculating a weighted sum of data point positions, where weights may include probability of each data point belonging to a particular cluster. These calculations may be repeated until convergence, whereby the distributions may not change much from iteration to iteration.

With continued reference to FIG. 1, prognostic chaining module 140 generates a cluster label for each of the defined number of clustering groups. A "cluster label" as used in this disclosure, includes a descriptor containing a summary of the topic of datapoints contained within each cluster and which distinguishes each cluster from one another. Cluster labels may be generated by comparing term distributions across clusters using techniques that may include feature selection such as mutual information and chi-squared feature selections. Terms that may contain low frequency and which may not represent the whole cluster may be omitted. Cluster labels may be generated by expert input whereby experts may provide input as to cluster features. These features may be utilized to retrieve k-nearest categorized expert inputs from which candidates for cluster labels may be extracted. Expert inputs regarding cluster labels may include expert submissions as well as textual submissions from journal articles and research papers. Candidates for cluster labels identified this way may be ranked such as by voting or fusion process. Cluster labels of several different clusters may be further combined to obtain better labels. For example, linear regression may be utilized to learn an optimal combination of labeler scores. Generating Gaussian mixture clustering model 152 includes assigning the first prognosis to a labeled cluster group and identifying a first causal link 156 contained within the labeled cluster group.

With continued reference to FIG. 1, prognostic chaining module 140 identifies a causal link chained to the first prognosis as a function of generating a Gaussian mixture clustering model 152. A "causal link" as used in this disclosure, includes a descriptor containing a root cause correlated to a prognosis. A "root cause" as used in this disclosure, includes an identifier as to why a user has a particular prognosis and what can be done to restore function. Root cause may include an analysis of deeper causes of particular medical conditions and symptoms. For instance and without limitation, a prognosis such as fibromyalgia may have a root cause that includes toxin exposure while a prognosis such as hypothyroidism may be due to digestive inflammation. Root cause may include a functional medicine centric approach that may use evidence based approaches to reverse chronic illness. For instance and without limitation, a prognosis such as frontal headache may be correlated to a causal link such as magnesium deficiency while a prognosis such as abdominal bloating may be correlated to a causal link such as small intestinal bacterial overgrowth (SIBO). In an embodiment, a prognosis may be correlated to one or more casual links. For instance and without limitation, a prognosis such as endometriosis may be correlated to a first causal link 156 such as progesterone deficiency and a second causal link such as impaired estrogen detoxification. Expert input may provide relative statistics and likelihoods of a prognosis being correlated to a particular causal link. For instance and without limitation, a prognosis such as hypothyroidism may be correlated to a first causal link 156 such as Hashimoto's thyroiditis that includes a sixty five percent likelihood and a second causal link such as impaired conversion of thyroxine (T4) to triiodothyronine (T3) that includes a twenty five percent likelihood.

With continued reference to FIG. 1, system 100 includes a causal link module 160 operating on a computing device. Causal link module 160 may include any hardware and/or software module. Causal link module 160 is configured to receive from prognostic chaining module 140 the first prognosis chained to the first causal link. Casual link module may receive first prognosis chained to first causal link 156 utilizing any network methodology as described throughout this disclosure. "Chaining" as used in this disclosure, includes linking a first prognosis to a first causal link. Linking may include attributing a cause for a prognosis to a particular causal link. For instance and without limitation, a first prognosis such as dysmenorrhea may be chained to a first causal link such as progesterone deficiency whereby dysmenorrhea may be attributed to being caused by progesterone deficiency. In yet another non-limiting example, a first prognosis such as colon cancer may be chained to a first causal link such as excess red meat consumption whereby colon cancer may be attributed to being caused by excess red meat consumption. Causal link module 160 may receive from prognostic chaining module 140 a second prognosis chained to a second causal link 164. Second prognosis may be generated from second user symptom datum as described above.

With continued reference to FIG. 1, causal link module 160 evaluates first causal link 156 and second causal link 164 to calculate a degree of similarity 168 between first causal link 156 and second causal link 164. Causal link module 160 may select first causal link 156 by determining that first causal link 156 matches the second causal link 164. Causal link module 160 may determine that first causal link 156 does not match the second causal link 164 and may display on a graphical user interface 120 a recommendation for further testing. Causal link module 160 is configured to receive from prognostic chaining module 140 a third prognosis chained to a third causal link. Casual link module 160 evaluates the first causal link 156 the second causal link 164 and the third causal link and selects the first causal link 156 and selects the first causal link 156 by determining that the first causal link 156 matches the second causal link 164 and the second causal link 164 matches the third causal link. Causal link module 160 may evaluate causal link by determining that the first causal link 156 does not match the second causal link 164 and the second causal link 164 matches the third causal link and select the second causal link 164. Causal link module 160 may evaluate causal links by receiving at least an expert input descriptor entered on a graphical user interface 120 operating on computing device containing a first causal link 156 probability score and a second causal link 164 probability score and selecting the first causal link 156 as a function of expert input descriptor.

"Causal link probability score" as used in this disclosure, includes expert input containing a probability percentage that a particular causal link is root cause of a prognosis. For instance and without limitation, first causal link 156 may contain a probability score of seventy two percent correlated to a first prognosis while second causal link 164 may contain a probability score of seventeen percent correlated to a second prognosis. In such an instance, causal link module 160 may select first causal link 156 because it contains a high percentage probability score as compared to second causal link 164.

With continued reference to FIG. 1, causal link module 160 is configured to calculate a degree of similarity 168 where the degree of similarity 168 includes a genetic factor multiplied by an environmental factor multiplied by an inactivity factor. A "genetic factor" as used in this disclosure, includes a description of a genetic cause that may attribute to a prognostic root cause. For instance and without limitation, a genetic factor may include a particular genetic sequence that may be inherited which predisposes a user to a genetic condition such as sickle cell disease or Alzheimer's disease. A genetic factor may include a particular single nucleotide polymorphism (SNP) and/or nucleotide sequence that may predispose a user to have a higher likelihood of developing particular conditions. An "environmental factor" as used in this disclosure, includes a description of an environmental cause that may attribute to a prognostic root cause. Environmental factors may include disease aggravators located in one's surroundings that may predispose a user to disease such as substance abuse, exposure to toxic chemicals, expose to ultraviolet radiation, exposure to bisphenol A (BPA), and the like. For instance and without limitation, an environmental factor may include a particular known environmental factor such as contaminated drinking water that may predispose a user to a particular prognosis such as estrogen dominance. An "inactivity factor" as used in this disclosure, includes a description of an inactivity cause that may attribute to a prognostic root cause. Inactivity factors may include disease aggravators due to the lack of physical movement and activity. For instance and without limitation, an inactivity factor may increase the likelihood of developing diseases that include cardiovascular disease, diabetes, obesity, colon cancer, high blood pressure, osteoporosis, lipid disorders, depression, anxiety and the like. In an embodiment, degree of similarity 168 may include a score for each factor that may contribute to overall similarity score. In an embodiment, causal link module 160 may evaluate total degree of similarity 168 calculated for each causal link and/or total degree of similarity 168 calculated for each factor.

Figure 2:
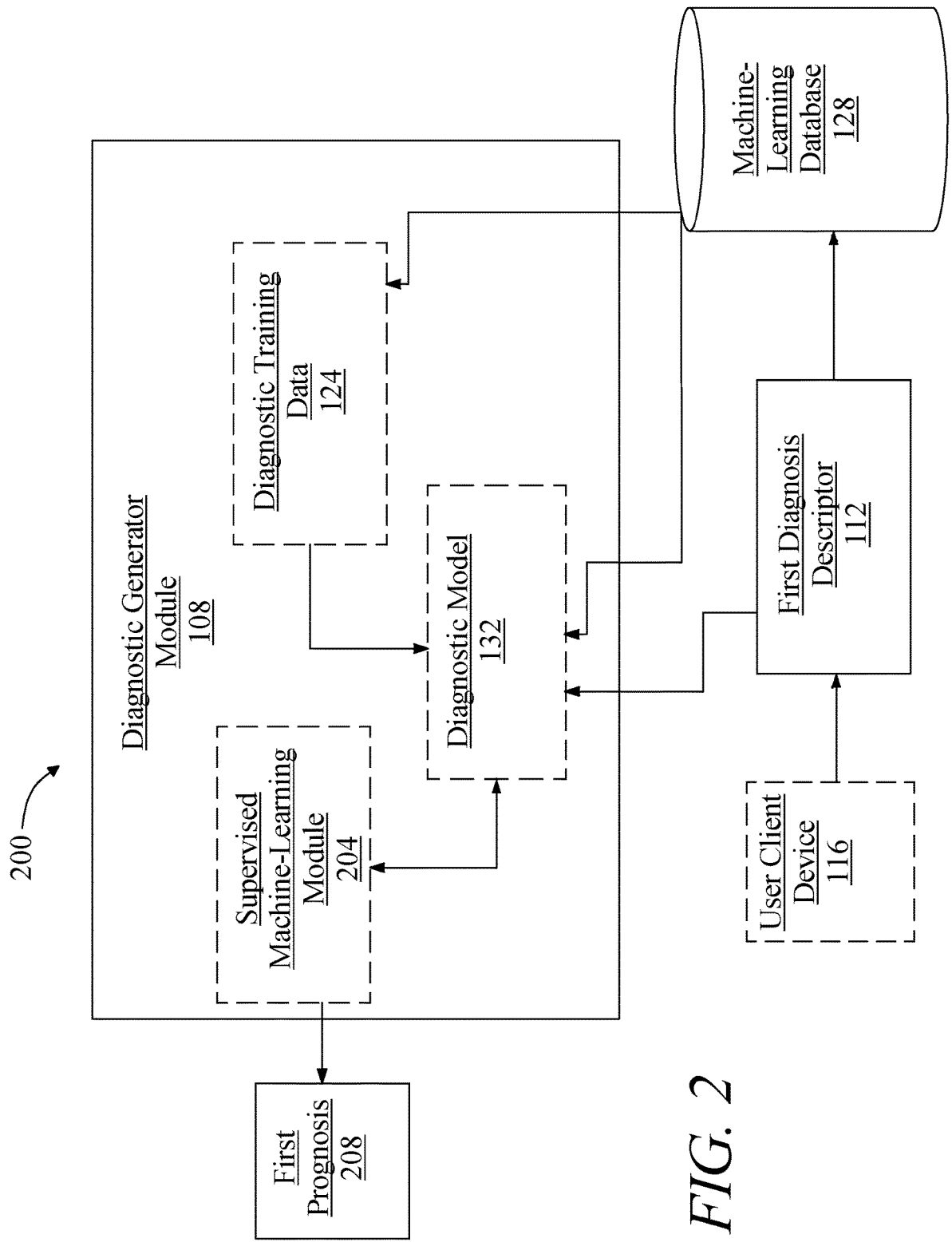
FIG. 2 is a block diagram illustrating an exemplary embodiment of a diagnostic generator module.

Referring now to FIG. 2, an exemplary embodiment 200 of diagnostic generator module 108 is illustrated. Diagnostic generator module 108 may be implemented as a hardware or software module. Diagnostic generator module 108 is configured to receive a first user symptom datum 112 from a user client device 116 wherein the first user symptom datum 112 includes a current medical indicator; receive diagnostic training data 124 from a machine-learning database 128 correlating symptom data to prognostic data; generate using a supervised machine-learning process a diagnostic model 132 that receives the first user symptom datum 112 as an input and produces an output containing a first prognosis.

With continued reference to FIG. 2, diagnostic generator module 108 receives a first user symptom datum 112 from a user client device 116, which may include any of the user client device 116 as described above in reference to FIG. 1. First user symptom datum 112 may include a description of the current state of health of a user. For instance and without limitation, first user symptom datum 112 may include a symptom that a user may be experiencing such as dry itchy eyes. In yet another non-limiting example, first user symptom datum 112 may include a medical concern a user may have such as an upset stomach after consuming dairy products. First user symptom datum 112 may include a description of a symptom user may be repeatedly experiencing, such as dizziness upon waking. First user symptom datum 112 may include a description of a symptom user may experience once such as acute onset chest pains. Diagnostic generator module 108 is configured to receive a first user blood test indicating at least a measure of user genetic data. First user blood test may include any of the user blood tests as described above in reference to FIG. 1. User genetic data may include any of the user genetic data as described above in reference to FIG. 1.

With continued reference to FIG. 2, diagnostic generator module 108 receives diagnostic training data 124 from a machine-learning database 128 correlating symptom data to prognostic data. Diagnostic generator module 108 may receive diagnostic training data 124 which contains symptom data correlated to prognostic data that matches symptom datum contained within a first user symptom datum 112. For instance and without limitation, a first user symptom datum 112 such as back pain may be utilized to select a diagnostic training set contained within machine-learning database 128 that contains symptom data that includes back pain correlated to prognostic data. In yet another non-limiting example, a first user symptom datum 112 such as shortness of breath may be utilized to select a diagnostic training set contained within machine-learning database 128 that includes symptom data that contains shortness of breath correlated to prognostic data. Diagnostic generator module 108 is configured to receive genetic training data which contains genetic data correlated to prognostic data. Diagnostic generator module 108 may match a user blood test containing a particular genetic sequence to genetic training data contained within machine-learning database 128 that contains the same genetic sequence correlated to prognostic data. For instance and without limitation, a first user blood test confirming the presence of the apolipoprotein E 4 (APOE4) gene may be utilized to select a genetic training data set that contains the APOE4 gene correlated to prognostic data.

With continued reference to FIG. 2, diagnostic generator module 108 may include supervised machine-learning module 204 that generates using a supervised machine-learning process a diagnostic model 132 that receives the first user symptom datum 112 as an input and produces an output containing a first prognosis 208. Supervised machine-learning module 204 may include any hardware or software module. Supervised machine-learning processes may include any of the supervised machine-learning processes as described above in reference to FIG. 1. Supervised machine-learning processes include algorithms that receive a training set relating a number of inputs to a number of outputs and seek to find one or more mathematical relationships between inputs to outputs, where each of the one or more mathematical relations is optimal according to some criterion specified to the algorithm using some scoring function. For instance, a supervised learning algorithm may use elements of symptom data as inputs, prognoses as outputs, and a scoring function representing a desired form of relationship to be detected between elements of symptom data and prognoses; scoring function may, for instance, seek to maximize the probability that a given element of symptom data and/or combination of elements of symptom data is not associated with a given prognosis and/or combination of prognoses. Scoring function may be expressed as a risk function representing an "expected loss" of an algorithm relating inputs to outputs, where loss is computed as an error function representing a degree to which a prediction generated by the relation is incorrect when compared to a given input-output pair provided in symptom training data. Persons skilled in the art, upon reviewing the entirety of this disclosure, will be aware of various possible variations of supervised machine-learning algorithms that may be used to determine relation between elements of symptom data and prognoses. In an embodiment, one or more supervised machine-learning algorithms may be restricted to a particular domain for instance, a supervised machine-learning process may be performed with respect to a given set of parameters and/or categories of parameters that have been suspected to be related to a given set of symptom data, and/or are specified as linked to a medical specialty and/or field of medicine covering a particular set of symptoms. As a non-limiting example, a particular set of prognoses may be linked to particular symptoms and a supervised machine-learning process may be performed to relate symptoms to prognoses; in an embodiment, domain restrictions of supervised machine-learning procedures may improve accuracy of resulting models by ignoring artifacts in training data. Domain restrictions may be suggested by experts and/or deduced from known purposes for particular evaluations and/or known treatments for particular diseases and/or stages of disease. Additional supervised learning processes may be performed without domain restrictions to detect, for instance, previously unknown and/or unsuspected relationships between symptom data and prognostic data. Supervised machine-learning module may be configured to generate diagnostic model 132 and/or genetic model as described above in more detail in reference to FIG. 1.

Figure 3:
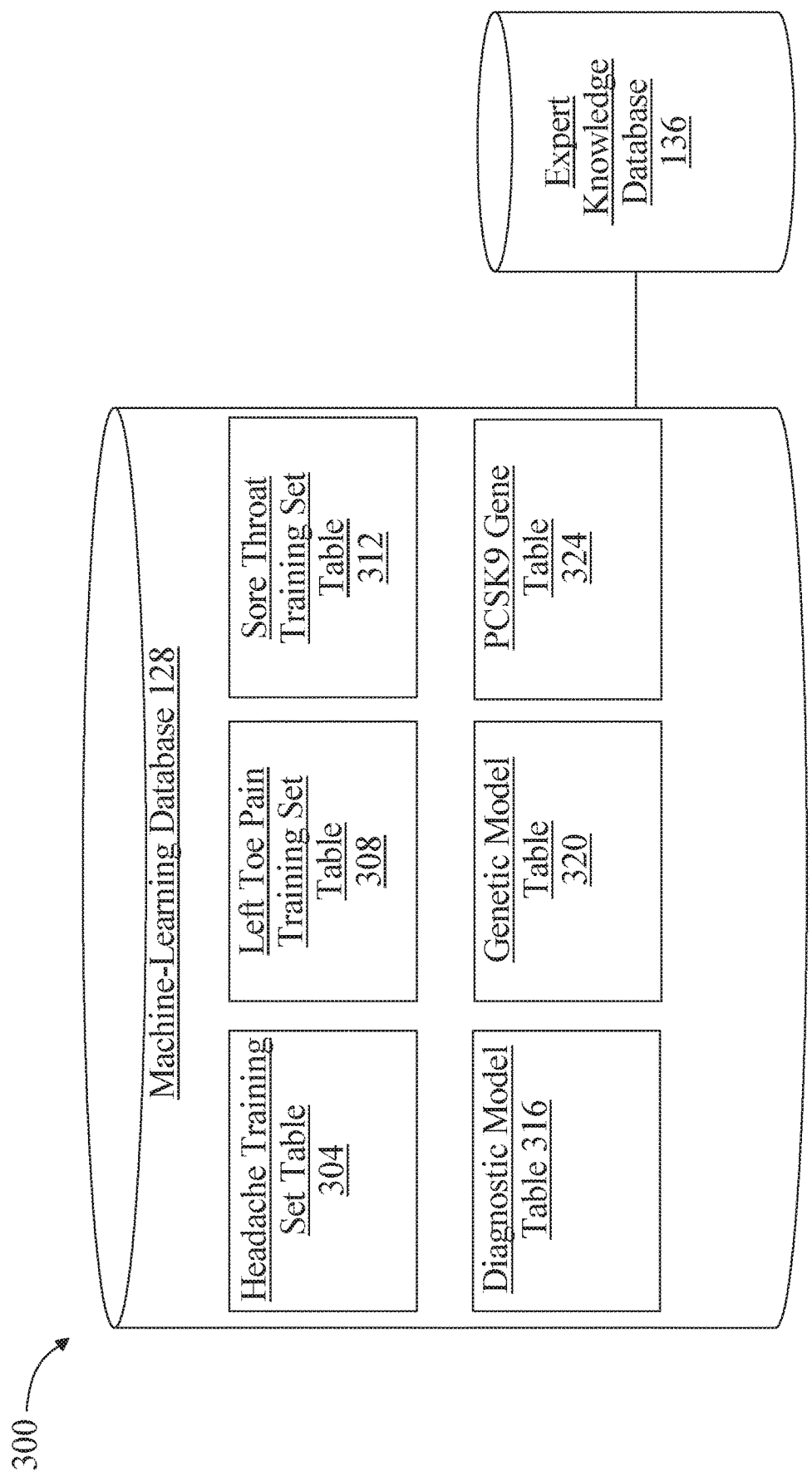
FIG. 3 is a block diagram illustrating an exemplary embodiment of a machine-learning database.

Referring now to FIG. 3, an exemplary embodiment 300 of machine-learning database 128 is illustrated. Machine-learning database 128 may include any data structure for ordered storage and retrieval of data, which may be implemented as a hardware or software module, and which may be implemented as any database structure suitable for use as machine-learning database 128 as described above in FIG. 1. One or more tables contained within machine-learning database 128 may include headache training set table 304; headache training set table 304 may include one or more data entries containing symptom data that includes a symptom such as headache correlated to prognostic data. One or more tables contained within machine-learning database 128 may include left toe pain table 308; left toe pain table 308 may include one or more data entries containing symptom data that includes a symptom such as left toe pain correlated to prognostic data. One or more tables contained within machine-learning database 128 may include sore throat table 312; sore throat table 312 may include one or more data entries containing symptom data that includes sore throat correlated to prognostic data. One or more tables contained within machine-learning database 128 may include diagnostic model table 316; diagnostic model table 316 may include one or more diagnostic models that may be utilized to generate a supervised machine-learning process. One or more tables contained within machine-learning database 128 may include genetic model table 320; genetic model table 320 may include one or more genetic models that may be utilized to generate a supervised machine-learning process. One or more tables contained within machine-learning database 128 may include proprotein convertase subtilisin kexin type 9 (PCSK9) table 324; PCSK9 table may include one or more data entries containing genetic data such as PCSK9 sequence correlated to prognostic data.

Figure 4:
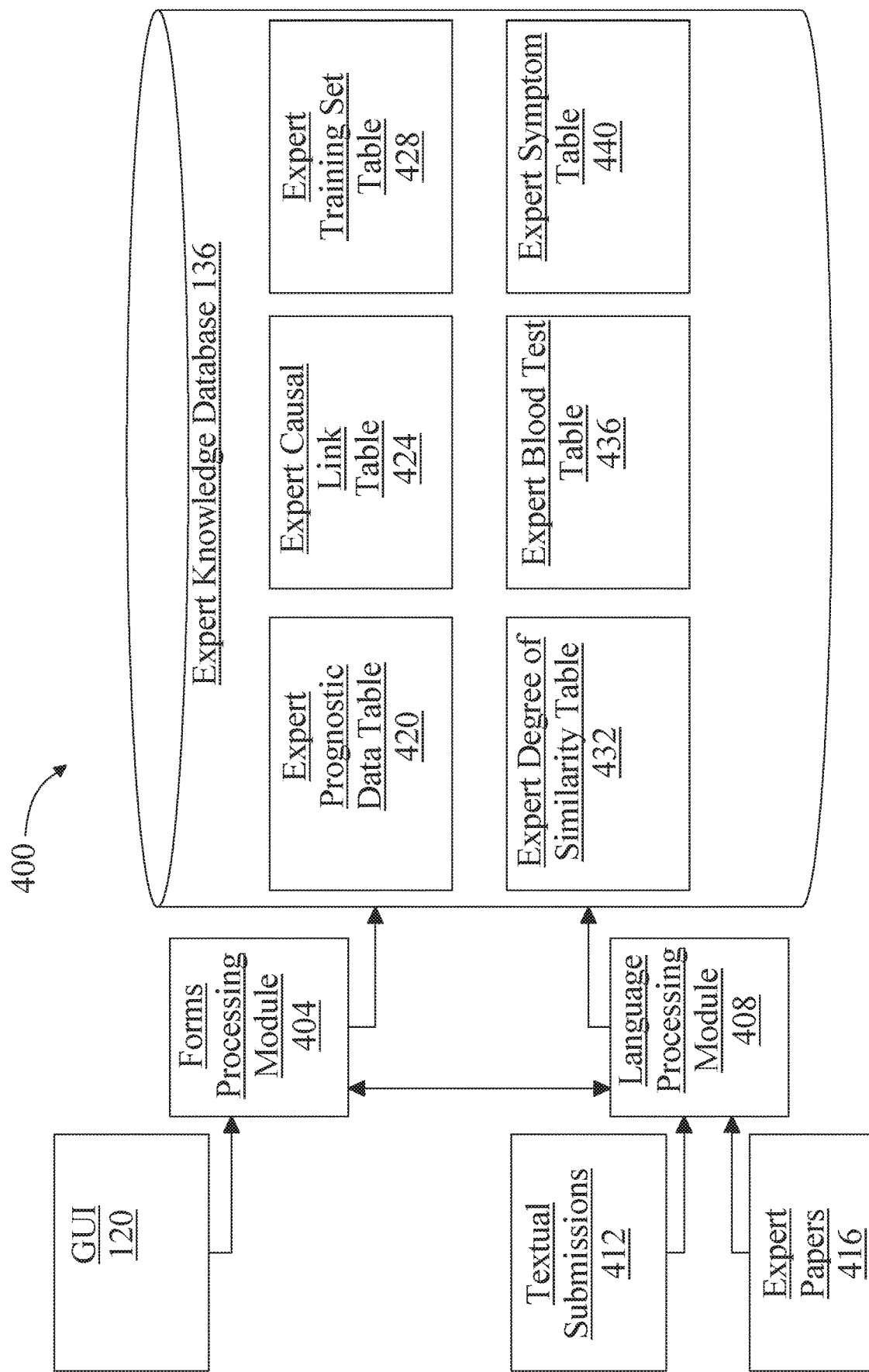
FIG. 4 is a block diagram illustrating an exemplary embodiment of an expert knowledge database.

Referring now to FIG. 4, an exemplary embodiment 400 of expert knowledge database 136 is illustrated. Expert knowledge database 136 may include any data structure for ordered storage and retrieval of data, which may be implemented as a hardware or software module, and which may be implemented as any database structure suitable for use as machine-learning database 128. Expert knowledge database 136 includes a forms processing module 404 that may sort data entered in a submission via graphical user interface 120 by, for instance, sorting data from entries in the graphical user interface 120 to related categories of data; for instance, data entered in an entry relating in the graphical user interface 120 to a symptom training data set may be sorted into variables and/or data structures for storage of symptom training data sets, while data entered in an entry relating to a symptom training set may be sorted into variables and/or data structures for the storage of, respectively, categories of symptom training data. Where data is chosen by an expert from pre-selected entries such as drop-down lists, data may be stored directly; where data is entered in textual form, language processing module 408 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 408 may indicate that entry should be treated as relating to a new label; this may be determined by, e.g., comparison to a threshold number of cosine similarity and/or other geometric measures of vector similarity of the entered text to a nearest existent label, and determination that a degree of similarity 168 falls below the threshold number and/or a degree of dissimilarity falls above the threshold number. Data from expert textual submissions 412, such as accomplished by filling out a paper or PDF form and/or submitting narrative information, may likewise be processed using language processing module 408. Data may be extracted from expert papers 416, which may include without limitation publications in medical and/or scientific journals, by language processing module 408 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

With continued reference to FIG. 4, one or more tables contained within expert knowledge database 136 may include expert prognosis table 420; expert prognosis table 420 may include any information provided by one or more experts regarding prognoses. One or more tables contained within expert knowledge database 136 may include expert causal link table 424; expert causal link table 424 may include any information provided by one or more experts regarding causal links. One or more tables contained within expert knowledge database 136 may include expert training set table 428; expert training set table 428 may include any information provided by one or more experts regarding training sets including diagnostic training sets and/or genetic training sets. One or more tables contained within expert knowledge database 136 may include expert degree of similarity 168 index table 432; expert degree of similarity index table 432 may include any information provided by one or more experts regarding degree of similarity 168. One or more tables contained within expert knowledge database 136 may include expert blood test table 436; expert blood test table 436 may include any information provided by one or more experts regarding blood test data. One or more tables contained within expert knowledge database 136 may include expert symptom table 440; expert symptom table 440 may include any information provided by one or more experts regarding symptom data.

Figure 5:
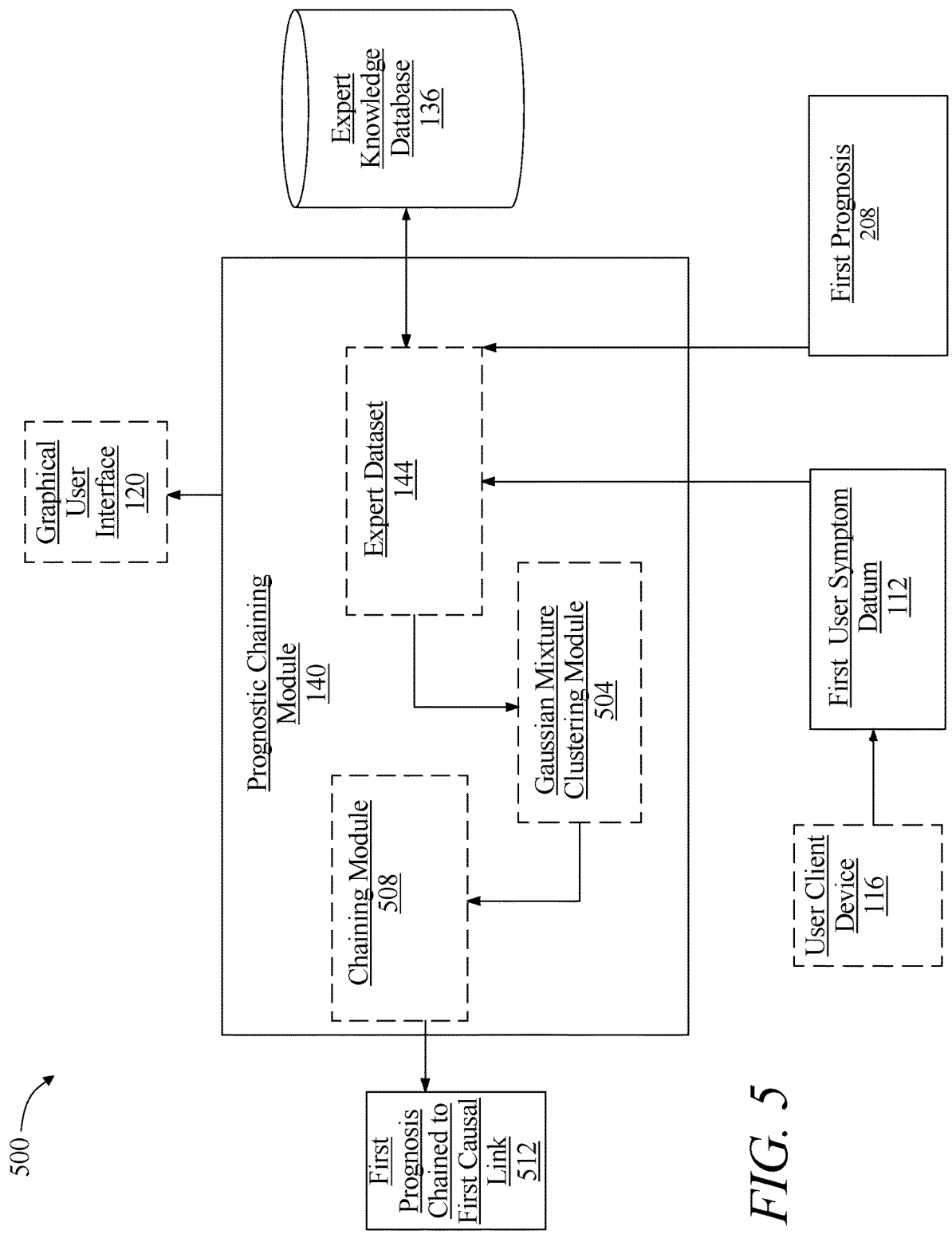
FIG. 5 is a block diagram illustrating an exemplary embodiment of a prognostic chaining module.

Referring now to FIG. 5, an exemplary embodiment 500 of prognostic chaining module 140 is illustrated. Prognostic chaining module 140 may be implemented as any hardware and/or software module. Prognostic chaining module 140 is configured to receive an expert input dataset 144 from an expert knowledge database 136 wherein the expert input dataset 144 further comprises prognostic data correlated to causal link data; receive the first user symptom datum 112 and the first prognosis 208 from the diagnostic generator module 108; generate a gaussian mixture clustering model 152 utilizing the expert input dataset 144 and the first prognosis 208 and outputting a defined number of clusters; and identify a first causal link 156 chained to the first prognosis 208 as a function of generating the gaussian mixture clustering model 152.

With continued reference to FIG. 5, prognostic chaining module 140 receives an expert input dataset 144 from expert knowledge dataset. Expert knowledge dataset includes data entries containing prognostic data correlated to causal link data. Prognostic data may include any of the prognostic data as described above in reference to FIG. 1. Causal link data may include any of the causal link data as described above in reference to FIG. 1. For instance and without limitation, expert knowledge dataset may include prognostic data such as coronary artery disease correlated to causal link data such as inflammation. In yet another non-limiting example, expert knowledge dataset may include a prognosis such as abdominal bloating correlated to causal link data such as small intestinal bacterial overgrowth (SIBO). In an embodiment, prognostic chaining module 140 may select expert knowledge dataset from expert knowledge database 136 by matching prognosis generated by diagnostic generator module 108 to an expert input dataset 144 containing the same prognosis. For instance and without limitation, a prognosis such as hypertension generated by diagnostic generator module 108 may be matched to an expert knowledge dataset that includes hypertension correlated to causal link data that includes magnesium deficiency. Expert knowledge dataset may be utilized as training data to generate gaussian mixture clustering module. Experts may provide inputs to expert knowledge database 136 regarding correlations of a prognosis to a causal link using any of the expert input methods as described above in reference to FIG. 4.

With continued reference to FIG. 5, prognostic chaining module 140 receives first user symptom datum 112 and first prognosis 208 from diagnostic generator module 108. Prognostic chaining module 140 may receive first user symptom datum 112 and first prognosis 208 utilizing any of the network methodologies as described herein.

With continued reference to FIG. 5, prognostic chaining module 140 may include Gaussian mixture clustering module 504 which may be implemented as any hardware or software module. Gaussian mixture clustering module 504 utilizes expert input dataset 144 and first prognosis 208 to output a defined number of clusters. Gaussian mixture clustering model 152 may include any of the Gaussian mixture clustering models 152 as described above in reference to FIG. 1. Gaussian mixture clustering module 504 generates a Gaussian mixture clustering model 152 by first selecting a defined number of clustering groups. In an embodiment, expert knowledge database 136 may contain information describing optimal number of clusters to be generated for a particular expert dataset. In an embodiment, prognostic chaining module 140 may receive expert dataset containing data describing the optimal number of clusters to be generated for the particular expert dataset. Gaussian mixture clustering module generates a cluster label for each of the defined number of clustering groups. Generating cluster labels may be performed by any of the methods as described above in reference to FIG. 1. Gaussian mixture clustering module 504 may assign first prognosis 208 to a labeled cluster group. This may be performed by calculating parameters that include both mean value and standard deviation as described above in more detail in reference to FIG. 1. Gaussian mixture clustering module 504 may generate EM algorithm to calculate mean value and standard deviation of each cluster as described above in reference to FIG. 1. Gaussian mixture clustering module 504 calculates distance of a datapoint to Gaussian center of each cluster as described above in more detail in FIG. 1. First prognosis 208 may then be utilized to identify a causal link contained within the labeled cluster group With continued reference to FIG. 5 prognostic chaining module 140 may include chaining module 508 which may be implemented as any hardware and/or software module. Chaining module 508 may identify a first causal link 156 chained to the first prognosis 208 as a function of generating the gaussian mixture clustering model 152. Gaussian mixture clustering module 504 may select a cluster based on generating Gaussian model that is closest in mean value and standard deviation to first prognosis 208. Prognostic chaining module 140 may identify within the selected cluster a first causal link 156 for first prognosis 208. In an embodiment, cluster label may contain a prognosis correlated to a causal link which may be utilized to identify a first casual link for first prognosis 208. For instance and without limitation, Gaussian mixture clustering module 504 may select a cluster that contains a cluster label for heart disease. Prognostic chaining module 140 may identify a first causal link 156 for heart disease contained within heart disease cluster. In an embodiment, heart disease cluster label may contain a first causal link 156 such as heavy metal toxicity that prognostic chaining module 140 may utilize to identify a first causal link. In an embodiment, prognostic chaining module 140 may identify a first causal link 156 based on datasets contained within heart disease cluster. For example, heart disease cluster may contain datasets containing heart disease prognosis correlated to first causal link. In such an instance, prognostic chaining module 140 may identify first causal link 156 by identifying first causal links contained within heart disease cluster. This may include performing additional classification algorithms that may include linear classifiers such as logistic regression, naïve bayes classifier, k-nearest neighbor, support vector machines, decision trees, boosted trees, random forest, neural networks, and the like. Prognostic chaining module 140 outputs first prognosis chained to first causal link 512.

Figure 6:
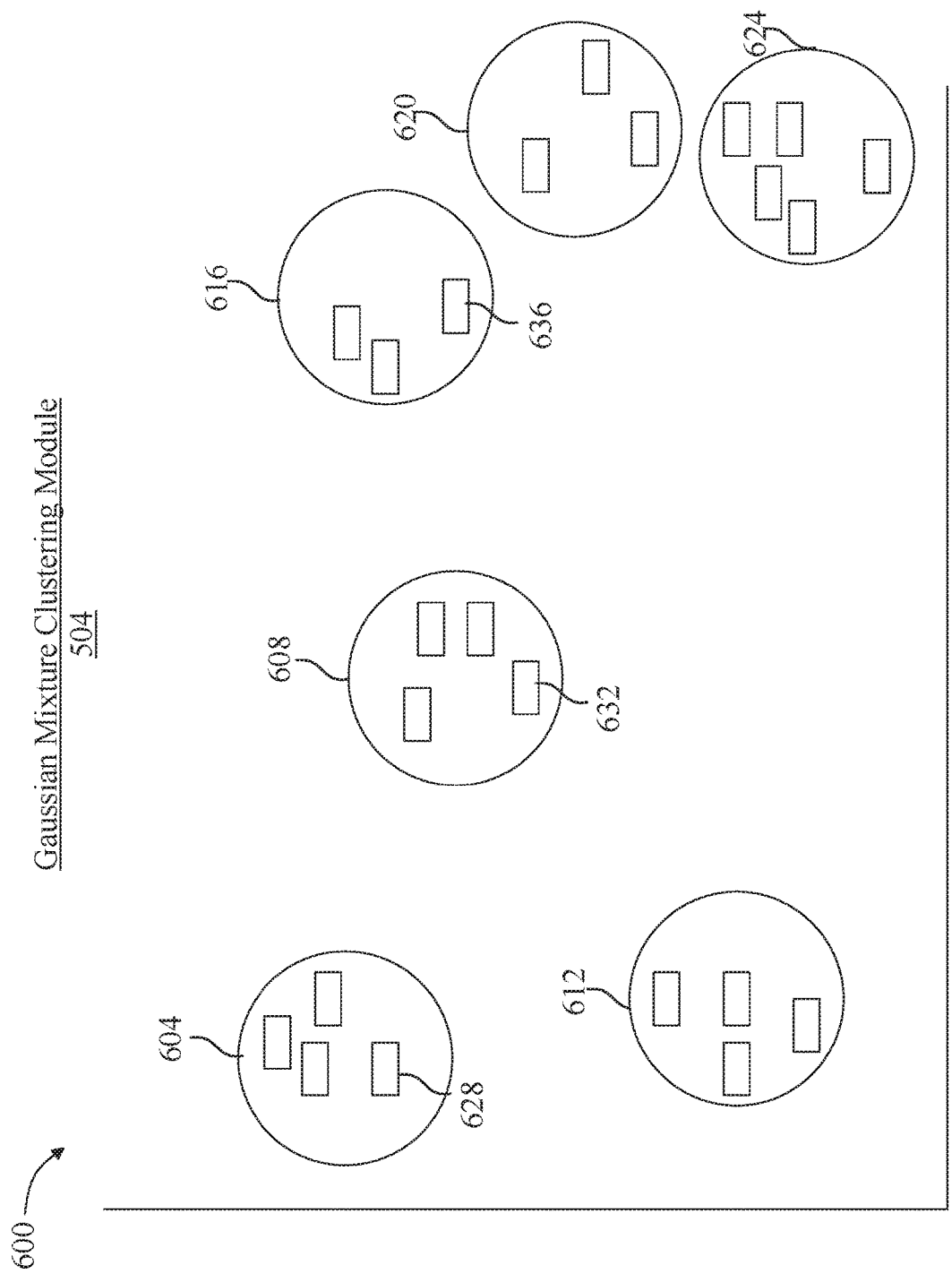
FIG. 6 is a diagrammatic representation of a Gaussian mixture clustering module.

Referring now to FIG. 6, an exemplary embodiment 600 of Gaussian mixture clustering algorithm is illustrated. Gaussian mixture clustering module 504 selects a defined number of clusters to generate. In an embodiment, gaussian mixture clustering module 504 may output six clustering which may include first cluster 604, second cluster 608, third cluster 612, fourth cluster 616, fifth cluster 620, and sixth cluster 624. Each of the six clusters may contain a cluster label which may be generated utilizing any of the methods as described above in reference to FIG. 1. First prognosis 208 may be assigned to a labeled cluster group based on mean value parameter and standard deviation parameter as described above in reference to FIG. 1. Each cluster of the defined number of clusters as calculated by Gaussian mixture clustering module may include one or more datapoints assigned to a particular cluster from expert input dataset 144. For example, first cluster 604 may contain datapoint 628. Datapoint 628 may include a prognosis correlated to a first causal link. In an embodiment, prognosis contained within datapoint 628 may match cluster label contained within first cluster 604. Second cluster 608 may contain datapoint 632 which may include a prognosis correlated to a first causal link. In an embodiment, prognosis contained within datapoint 632 may match cluster label contained within second cluster 608. Fourth cluster 616 may contain datapoint 636 which may include a prognosis correlated to a first causal link. In an embodiment, prognosis contained within datapoint 636 may match cluster label contained within fourth cluster 616.

Figure 7:
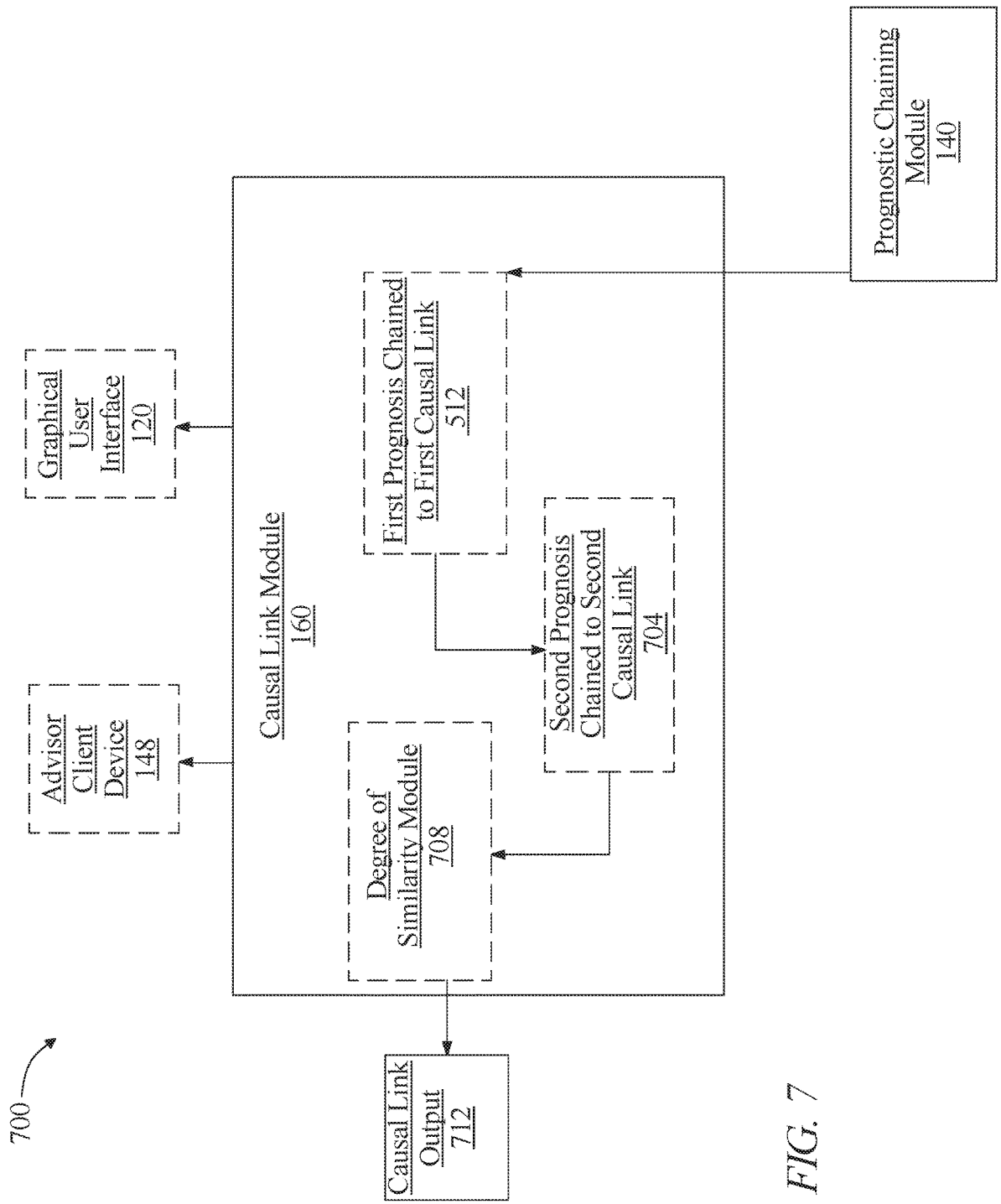
FIG. 7 is a block diagram illustrating an exemplary embodiment of a causal link module.

Referring now to FIG. 7, an exemplary embodiment 700 of causal link module 160 is illustrated. Causal link module 160 may be implemented as any hardware and/or software module. Causal link module 160 receives first prognosis chained to first causal link 512 from prognostic chaining module 140. Causal link module 160 is configured to receive second prognosis chained to second causal link 704. Second prognosis chained to second causal link 704 may be generated utilizing any of the methods as described above in reference to generating first prognosis 208 and/or first prognosis chained to first causal link 512. Causal link module 160 may include degree of similarity module 708 which may be implemented as any hardware and/or software module. Degree of similarity module 708 evaluates a first causal link 156 and second causal link 164 to calculate a degree of similarity 168 between first causal link 156 and second causal link 164. Causal link module 160 may select a causal link after evaluating a plurality of causal link where a causal link output 712 may be displayed on a graphical user interface 120. Causal link module 160 may display causal link output 712 on advisor client device 148. Causal link module 160 evaluates first causal link 156 and second causal link 164 and determines if the first causal link 156 matches the second causal link 164. For instance and without limitation, causal link module 160 may evaluate a first prognosis 208 such as heart disease linked to a first causal link 156 of heavy metal toxicity to a second prognosis such as brain fog linked to a second causal link 164 of heavy metal toxicity. Causal link module 160 evaluates first causal link 156 of heavy metal toxicity and compares it to second causal link 164 of heavy metal toxicity to determine that the two match. Causal link module 160 may then generate a causal link output 712 of heavy metal toxicity that may be displayed on graphical user interface 120 and/or advisor client device 148. Causal link module 160 may evaluate a first causal link 156 and a second causal link 164 and determine that the first causal link 156 does not match the second causal link 164. For instance and without limitation, causal link module 160 may evaluate a first prognosis 208 such as high blood pressure chained to a first causal link 156 such as magnesium deficiency and a second prognosis such as hypothyroidism chained to a second causal link 164 such as selenium deficiency. In such an instance, causal link module 160 determines that first causal link 156 containing magnesium deficiency does not match second causal link 164 of selenium deficiency. In such an instance, causal link module 160 may display on graphical user interface 120 a recommendation for further testing whereby additional blood tests and/or medical imaging and diagnostics may be needed to be performed by a medical professional to evaluate why nutritional deficiencies are occurring within the body. Causal link module 160 may receive expert input through graphical user interface 120 when a first causal link 156 does not match a second causal link 164. In an embodiment, when first causal link 156 does not match second causal link 164, causal link module 160 may display first prognosis chained to first causal link 156 and second prognosis chained to second causal link 164 on graphical user interface 120. In such an instance, an expert, including any of the experts as described above, may enter a first causal link 156 probability score and a second causal link 164 probability score. "Matching" as used in this disclosure, includes a first causal link that is not identical to a second causal link. For instance and without limitation, a first causal link such as rheumatoid arthritis matches a second causal link such as rheumatoid arthritis. A first causal link such as mold toxicity does not match a second causal link such as estrogen dominance. A "causal link probability score" as used in this disclosure, includes a numerical score indicating the likelihood of a particular causal link being a cause of a prognosis. Causal link probability score may be generated by an expert, who may review a prognosis and associated medical records and determine the likelihood that a prognosis is attributed to a causal link. Causal link module 160 may select a causal link as a function of expert input descriptor containing causal link probability score. For instance and without limitation, causal link module 160 may receive an expert input descriptor entered on graphical user interface 120 containing a first causal link 156 probability score for a first causal link 156 of mercury poisoning with a 73% probability and a second causal link 164 of aluminum toxicity with a 4% probability and select first causal link 156 based on first causal link probability score.

With continued reference to FIG. 7, causal link module 160 is configured to receive from prognostic chaining module 140 a third prognosis chained to a third causal link. Third prognosis chained to a third causal link may be generated utilizing any of the methods as described above for generating first prognosis 208 generated to first causal link. Causal link module 160 may evaluate the first causal link 156 and the second causal link 164 and the third causal link. Causal link module 160 may generate a causal link output 712 by determining the first causal link 156 matches the second causal link 164 and the second causal link 164 matches the third causal link. For instance and without limitation, causal link module 160 may evaluate a first prognosis 208 such as hypothyroidism chained to a first causal link 156 such as gluten intolerance, a second prognosis such as endometriosis chained to a first causal link 156 such as gluten intolerance, and a third prognosis such as multiple sclerosis chained to a third causal link such as gluten intolerance. Causal link module 160 may evaluate the first causal link 156 containing gluten intolerance, second causal link 164 containing gluten intolerance, and third causal link containing gluten intolerance and generate causal link output 712 that contains gluten intolerance. Causal link module 160 may determine that first causal link 156 does not match second causal link 164 and the second causal link 164 matches the third causal link and thereby select second causal link 164 as causal link output 712. For instance and without limitation, causal link module 160 may receive a first prognosis 208 such as type 2 diabetes mellitus chained to a first causal link 156 of food addiction, a second prognosis such as dysmenorrhea chained to a second causal link 164 of estrogen dominance, and a third prognosis such as breast cancer chained to a third causal link of estrogen dominance. Causal link module 160 may determine that the first causal link 156 of food addiction does not match the second causal link 164 of estrogen dominance and that the second causal link 164 of estrogen dominance does match the third causal link of estrogen dominance. In such an instance, causal link module 160 may select estrogen dominance as causal link output 712.

With continued reference to FIG. 7, causal link module 160 may include degree of similarity 168 module which may calculate degree of similarity 168. Degree of similarity 168 may include a genetic factor multiplied by an environmental factor multiplied by an inactivity factor. Factors may include any of the factors as described above in reference to FIG. 1. Degree of similarity 168 may indicate how similar a causal link may be to another causal link that do not match. For instance and without limitation, causal link module 160 may determine that a first causal link 156 such as heavy metal toxicity does not match a second causal link 164 such as impaired estrogen detoxification. Degree of similarity 168 module may generate a degree of similarity 168 value for heavy metal toxicity and impaired estrogen detoxification. In such an instance, degree of similarity 168 index value may reflect a shared environmental factor such as fluoride contamination in water that may be attributing to heavy metal toxicity and impaired estrogen detoxification. In such an instance, causal link module 160 may generate causal link output 712 that contains fluoride contamination.

Figure 8:
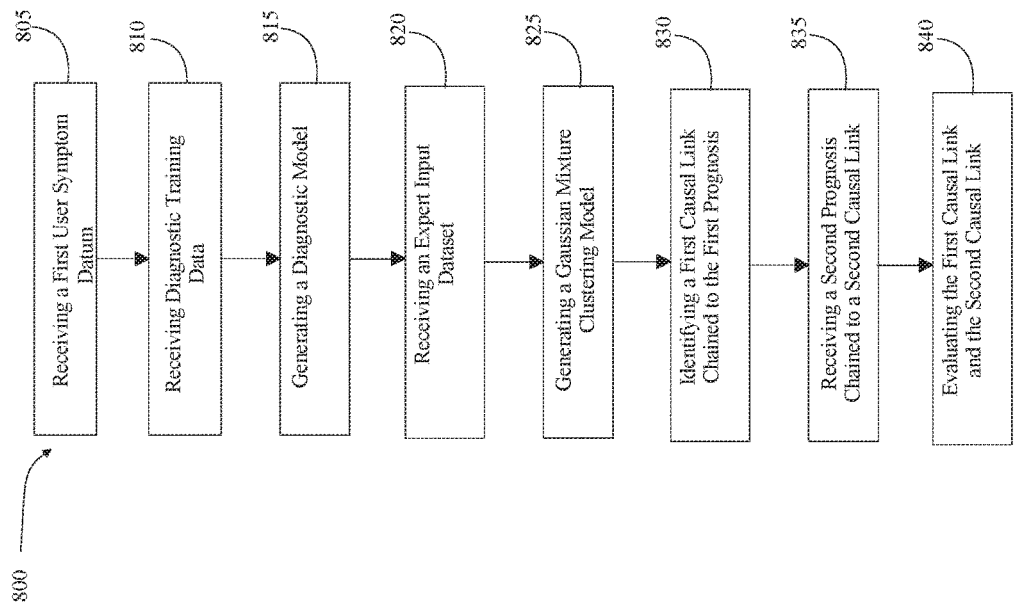
FIG. 8 is a process flow diagram illustrating an exemplary embodiment of a method of identifying a causal link.

Referring now to FIG. 8, an exemplary embodiment of a method 800 of identifying a causal link is illustrated. At step 805 a computing device receives a first user symptom datum 112 from a user client device 116 wherein the first user symptom datum 112 includes a current medical indicator. Computing device may include any of the computing devices as described herein. First user symptom datum 112 includes any of the user symptom datums as described above in reference to FIGS. 1-8. For instance and without limitation, first user symptom datum 112 may include a description of a particular symptom that a user is experiencing. For example, first user symptom datum 112 may include a description of sharp left sided abdominal pain that a user experiences after eating. First user symptom datum 112 may include a description of a recurrent symptom that a user may experience, such as tingling in fingers and toes upon waking. Computing device is configured to receive a first user blood test indicating at least a measure of user genetic data. First user blood test may include any of the user blood tests as described above in reference to FIG. 1. For example, first user blood test may include a genetic sample containing two copies of the MSH6 gene that causes Lynch syndrome. Computing device may receive first user symptom datum 112 utilizing any network methodology as described herein.

With continued reference to FIG. 8, at step 810 computing device receives diagnostic training data 124 from a machine-learning database 128 correlating symptom data to prognostic data. Diagnostic training data 124 may include any of the diagnostic training data 124 as described above in reference to FIGS. 1-8. Diagnostic training data 124 may be received utilizing any network transmission methodology as described herein. Diagnostic training data 124 includes symptom data correlated to prognostic data. Symptom data may include any of the symptom data as described above in reference to FIGS. 1-8. Prognostic data may include any of the prognostic data as described above in reference to FIGS. 1-8. For instance and without limitation, diagnostic training data 124 may include symptom data such as sore throat correlated to prognostic data such as strep throat. In yet another non-limiting example, diagnostic training data 124 may include symptom data such as fatigue correlated to prognostic data such as Chronic fatigue syndrome. Computing device may receive diagnostic training data 124 that contains symptom data that matches first user symptom datum 112. For instance and without limitation, first user symptom datum 112 that contains ringing in the ears may be matched to diagnostic training data 124 that contains symptom data that includes ringing in the ears. Computing device receives genetic training data from machine-learning database correlating genetic data to prognostic data. Genetic training data may include any of the genetic training data as described above in reference to FIGS. 1-8. Genetic data may include any of the genetic data as described above in reference to FIGS. 1-8. Prognostic data may include any of the prognostic data as described above in reference to FIGS. 1-8. For instance and without limitation, genetic training data may include genetic data such as apolipoprotein e 4 (APOE4) correlated to prognostic data such as heart disease.

With continued reference to FIG. 8, at step 815 computing device generates using a supervised machine-learning process a diagnostic model 132 that receives a first user symptom datum 112 as an input and produces an output containing a first prognosis 208. Supervised machine-learning process may include any of the supervised machine-learning processes as described above in reference to FIGS. 1-8. Generating supervised machine-learning process may be performed by supervised machine-learning module 204 operating on diagnostic generator module 108. Computing device is configured to generate a genetic model that receives first user genetic data as an input and produces an output containing a first prognosis 208. This may be performed by any of the methods as described above in reference to FIGS. 1-8.

With continued reference to FIG. 8, at step 820 computing device receives an expert input dataset 144 from expert knowledge database 136 wherein the expert input dataset 144 includes prognostic data correlated to causal link data. Computing device may receive expert input dataset 144 utilizing any of the network transmission methods as described herein. Exert input dataset may be generated based on expert inputs as described above in reference to FIGS. 1-8. Expert input dataset 144 may include a plurality of datapoints containing prognostic data correlated to causal link data. For instance and without limitation, expert input dataset 144 may include prognostic data such as heart disease correlated to causal link data such as heavy metal toxicity. In yet another non-limiting example, expert input dataset 144 may include prognostic data such as hypothyroidism correlated to causal link data such as low iodine levels. Expert input dataset 144 may be organized and maintained within exert knowledge database as described above in more detail in reference to FIG. 4.

With continued reference to FIG. 8, at step 825 computing device generates a Gaussian mixture clustering model 152 utilizing the expert input dataset 144 and the first prognosis 208 and outputting a defined number of clusters. Generating Gaussian mixture clustering model 152 may be performed utilizing any of the methods as described above in reference to FIGS. 1-8. Generating Gaussian mixture clustering model 152 includes selecting a defined number of clustering groups. Computing device may select number of clustering groups based on expert inputs as described above in more detail in reference to FIGS. 1-8. Upon determining defined number of clustering groups, computing device generates a cluster label for each of the defined number of clustering groups. Cluster labels may be generated utilizing any of the methods as described above in reference to FIG. 1. Computing device assigns a first prognosis 208 to a labeled cluster group, which may be performed based on calculations of mean value parameters and standard deviation parameters as described above in more detail in reference to FIGS. 1-8. Computing device identifies a first causal link 156 contained within the labeled cluster group. In an embodiment, cluster label may include a prognosis and correlated causal link which may be utilized to identify a first causal link. In an embodiment, computing device may perform additional classifying algorithms that may be utilized to identify a first causal link 156 as described above in more detail in reference to FIGS. 1-8.

With continued reference to FIG. 8, at step 830 computing device identifies a first causal link 156 chained to first prognosis as a function of generating Gaussian mixture clustering model 152. This may be performed utilizing any of the methods as described above in reference to FIGS. 1-8.

With continued reference to FIG. 8, at step 835 computing device receives a second prognosis chained to second causal link 164. Computing device may receive second prognosis utilizing any network transmission methodology as described above in reference to FIGS. 1-8. Second prognosis chained to second causal link 164 may be generated by receiving a second user symptom datum from a user client device 116 wherein the second user symptom datum includes a current medical indicator, receiving diagnostic training data 124 from a machine-learning database 128 correlating symptom data to prognostic data, generating using a supervised machine-learning process a diagnostic model 132 that receives the second user symptom datum as an input and produces an output containing second prognosis.

With continued reference to FIG. 8, at step 840 computing device evaluates the first causal link 156 and the second causal link 164 to calculate a degree of similarity 168 between first causal link 156 and the second causal link 164. Degree of similarity 168 includes any of the degree of similarity 168 as described above in reference to FIGS. 1-8. Degree of similarity 168 may be calculated according to any of the methods as described above in reference to FIGS. 1-8. Evaluating first causal link 156 and second causal link 164 may be performed utilizing any of the methods as described above in reference to FIG. 7. Computing device may receive a third prognosis chained to a third causal link. Computing device may evaluate the third causal link by evaluating the first causal link 156 and the second causal link 164 and the third causal link and selecting the first causal link 156 by determining that the first causal link 156 matches the second causal link 164 and the second causal link 164 matches the third causal link. In an embodiment, computing device may display on graphical user interface 120 a recommendation for a medical professional to engage in further testing such as when first causal link 156 does not match second causal link 164.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
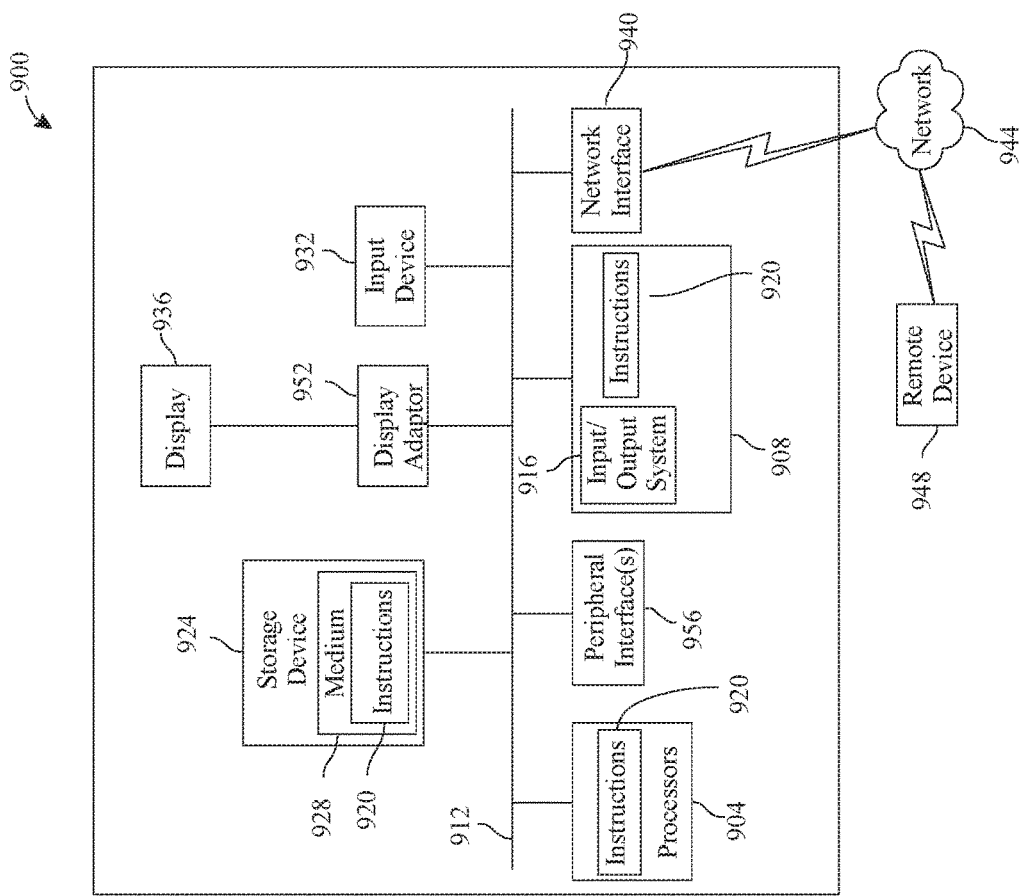
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Memory 908 may include various components (e.g., machine-readable media) including, but not limited to, a random access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for identifying a causal link including a computing device wherein the computing device further comprises one or more network interfaces and one or more processors, the system comprising:
   a diagnostic generator module operating on the computing device, the diagnostic generator module designed and configured to:
      receive a first user symptom datum from a user client device associated with a user wherein the first user symptom datum includes a current medical indicator;
      receive diagnostic training data from a machine-learning database correlating symptom data to prognostic data; and
      generate, using a supervised machine-learning process, a diagnostic model that receives the first user symptom datum as an input and produces an output containing a first prognosis;
   a prognostic chaining module operating on the computing device, the prognostic chaining module designed and configured to:
      receive an expert input dataset from an expert knowledge database wherein the expert input dataset comprises an expert journal article identifying prognostic data correlated to causal link data;
      receive the first user symptom datum and the first prognosis from the diagnostic generator module;
      generate a gaussian mixture clustering model utilizing the expert input dataset and the first prognosis and outputting a defined number of clusters; and
      identify a first causal link associated with the user chained to the first prognosis as a function of generating the gaussian mixture clustering model; and
   a causal link module operating on the computing device, the causal link module designed and configured to:
      receive from the prognostic chaining module the first prognosis chained to the first causal link associated with the user, wherein the first causal link identifies a root cause of the first prognosis;
      receive from the prognostic chaining module a second prognosis chained to a second causal link associated with the user, wherein the second causal link identifies a root cause of the second prognosis; and
      evaluate the first causal link and the second causal link to calculate a degree of similarity between the first causal link and the second causal link, wherein evaluating the first causal link and the second causal link comprises generating a recommendation for further testing as a function of the degree of similarity and displaying the recommendation for further testing at an advisor client device.

2. The system of claim 1, wherein the diagnostic generator module is further configured to:
   receive a first user blood test indicating a measure of user genetic data;
   receive genetic training data from a machine-learning database correlating genetic data to prognostic data; and
   generate, using a supervised machine-learning process, a genetic model that receives the first user blood test indicating the measure of user genetic data as an input and produces an output containing a first prognosis.

3. The system of claim 1, wherein generating the gaussian mixture clustering model further comprises:
   selecting a defined number of clustering groups;
   generating a cluster label for each of the defined number of clustering groups;
   assigning the first prognosis to a labeled cluster group; and
   identifying a first causal link contained within the labeled cluster group.

4. The system of claim 1, wherein receiving a second prognosis chained to a second causal link further comprises:
   receiving a second user symptom datum from a user client device wherein the second user symptom datum includes a current medical indicator;
   receiving diagnostic training data from a machine-learning database correlating symptom data to prognostic data;
   generating, using a supervised machine-learning process a diagnostic model that receives the second user symptom datum as an input and produces an output containing a second prognosis; and identifying a second causal link chained to the second prognosis as a function of generating a gaussian mixture clustering model.

5. The system of claim 1, wherein the causal link module is further configured to select the first causal link by determining that the first causal link matches the second causal link.

6. The system of claim 1, wherein the causal link module is further configured to determine that the first causal link does not match the second causal link.

7. The system of claim 1, wherein the causal link module is further configured to:
   receive from the prognostic chaining module a third prognosis chained to a third causal link;
   evaluate the first causal link and the second causal link and the third causal link; and
   select the first causal link by determining that the first causal link matches the second causal link and the second causal link matches the third causal link.

8. The system of claim 7 further comprising:
   determining that the first causal link does not match the second causal link and the second causal link matches the third causal link; and
   selecting the second causal link.

9. The system of claim 1, wherein evaluating the first causal link further comprises:
   receiving at least an expert input descriptor entered on a graphical user interface operating on the computing device containing a first causal link probability score and a second causal link probability score; and
   selecting the first causal link as a function of the expert input descriptor.

10. The system of claim 1, wherein the degree of similarity further comprises a genetic factor multiplied by an environmental factor multiplied by an inactivity factor.

11. A method of identifying a causal link, the method comprising:
   receiving, by a computing device associated with a user, a first user symptom datum from a user client device wherein the first user symptom datum includes a current medical indicator;
   receiving by the computing device diagnostic training data from a machine-learning database correlating symptom data to prognostic data;
   generating by the computing device, using a supervised machine-learning process, a diagnostic model that receives the first user symptom datum as an input and produces an output containing a first prognosis;
   receiving by the computing device an expert input dataset from an expert knowledge database wherein the expert input dataset comprises an expert journal article identifying prognostic data correlated to causal link data;
   generating by the computing device a gaussian mixture clustering model utilizing the expert input dataset and the first prognosis and outputting a defined number of clusters;
   identifying by the computing device a first causal link chained to the first prognosis as a function of generating the gaussian mixture clustering model associated with the user, wherein the first causal link identifies a root cause of the first prognosis;
   receiving by the computing device a second prognosis chained to a second causal link associated with the user, wherein the second causal link identifies a root cause of the second prognosis; and
   evaluating by the computing device the first causal link and the second causal link to calculate a degree of similarity between the first causal link and the second causal link, wherein evaluating the first causal link and the second causal link comprises generating a recommendation for further testing as a function of the degree of similarity and displaying the recommendation for further testing at an advisor client device.

12. The method of claim 11, wherein receiving the first user symptom datum further comprises:
   receiving a first user blood test indicating a measure of user genetic data;
   receiving genetic training data from a machine-learning database correlating genetic data to prognostic data; and
   generating, using a supervised machine-learning process, a genetic model that receives the first user blood test indicating the measure of user genetic data as an input and produces an output containing a first prognosis.

13. The method of claim 11, wherein generating the gaussian mixture clustering model further comprises:
   selecting a defined number of clustering groups;
   generating a cluster label for each of the defined number of clustering groups;
   assigning the first prognosis to a labeled cluster group; and
   identifying a first causal link contained within the labeled cluster group.

14. The method of claim 11, wherein receiving a second prognosis chained to a second causal link further comprises:
   receiving a second user symptom datum from a user client device wherein the second user symptom datum includes a current medical indicator;
   receiving diagnostic training data from a machine-learning database correlating symptom data to prognostic data;
   generating using a supervised machine-learning process a diagnostic model that receives the second user symptom datum as an input and produces an output containing a second prognosis; and
   identifying a second causal link chained to the second prognosis as a function of generating a gaussian mixture clustering model.

15. The method of claim 11, wherein evaluating the first causal link further comprises selecting the first causal link by determining that the first causal link matches the second causal link.

16. The method of claim 11, wherein evaluating the first causal link further comprises
   determining that the first causal link does not match the second causal link.

17. The method of claim 11, wherein evaluating the first causal link further comprises:
   receiving a third prognosis chained to a third causal link;
   evaluating the first causal link and the second causal link and the third causal link; and
   selecting the first causal link by determining that the first causal link matches the second causal link and the second causal link matches the third causal link.

18. The method of claim 17 further comprising:
   determining that the first causal link does not match the second causal link and the second causal link matches the third causal link; and
   selecting the second causal link.

19. The method of claim 11, wherein evaluating the first causal link further comprises:
   receiving at least an expert input descriptor entered on a graphical user interface operating on the computing device containing a first causal link probability score and a second causal link probability score; and selecting the first causal link as a function of the expert input descriptor.

20. The method of claim 11, wherein calculating the degree of similarity further comprises a genetic factor multiplied by an environmental factor multiplied by an inactivity factor.

\* \* \* \* \*